United States Patent [19]

Delbard

[11] Plant 4,671

[45] Mar. 17, 1981

[54] ROSE PLANT

[75] Inventor: Georges Delbard, Paris, France

[73] Assignee: Armstrong Nurseries, Inc., Ontario, Calif.

[21] Appl. No.: 108,159

[22] Filed: Dec. 28, 1979

[51] Int. Cl.[3] ..... A01H 5/00
[52] U.S. Cl. ..... Plt./18
[58] Field of Search ..... Plt./18

*Primary Examiner*—Robert E. Bagwill

*Attorney, Agent, or Firm*—William H. Elliott, Jr.; Andrew R. Klein

[57] ABSTRACT

A new variety of rose plant of the hybrid Tea class, being a hardy outdoor tall bush seedling, particularly adapted for garden decoration. Medium large, well formed buds and blooms are borne mostly in clusters on long strong stems. Overall color effect is light lavender. Vigorous new growth clothed with large somewhat leathery foliage supports long blooming cycle through most of growing season.

1 Drawing Figure

This invention relates to a new class of hybrid Tea rose. The plant is a seedling of the hardy, tall bushy outdoor type, cultivated for garden decoration. It was first propagated in Evry, France, but the plant described herein was one derived from budwood of that propagation, and was grown in Ontario, Calif. References to the growth and behavior of the plant pertain to plants raised in Southern California.

The new variety was propagated by Georges Delbard in Evry, France, having as its seed parent "(Holstein × Bayadère) × Prelude" and, as its pollen parent, "Saint-Exupery". It holds its distinguishing characteristics through succeeding propagations by budding.

The new variety sometimes bears its flowers singly, but usually two to four blooms are carried on one stem, in irregular clusters. The stems are strong and long. The plant blooms freely outdoors, and nearly continuously during the growing season. Its fragrance is a strong blend of citrus and tea.

This new cultivar may most readily be distinguished in the following ways from the named cultivars in the ancestry of its seed parent, which itself is an unnamed, undisseminated seedling:

Holstein bears flowers with six petals of crimson coloration, whereas the new rose bears flowers of significantly greater petalage (from 25 to 30) and a light lavender coloration. Further, Holstein is classified as a hybrid floribunda, whereas the new cultivar is classified as a hybrid tea.

Bayadère bears flowers with significantly more petals (from 50 to 55) of salmon pink coloration suffused with yellow, whereas the new rose bears flowers of from 25 to 30 petals which are of light lavender coloration essentially as described and illustrated herein. Further, Bayadère has only a slight fragrance, whereas the new rose has a very strong fragrance.

Prelude bears flowers of 25 petals, whereas the new rose bears flowers of significantly more petals (from 25 to 30), with up to 5 additional petaloids. Further, Prelude has significantly softer foliage than the hard, leathery foliage of the new cultivar.

This new cultivar may most readily be distinguished from its pollen parent, Saint-Exupery, by the following combination of characteristics:

Whereas the new cultivar bears open flowers of from 3½ to 4½ inches diameter, Saint-Exupery bears significantly larger open flowers which are 5 inches in diameter.

Whereas Saint-Exupery has flowers of only slight fragrance, the new rose has flowers of significantly stronger fragrance.

Saint-Exupery usually bears flowers singly on a stem, whereas the new cultivar usually bears flowers in clusters of from 2 to 4 on a stem.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is average in length and average to heavy in caliper, being erect, stiff and almost smooth, with some stipitate glands. The color is between Brilliant Yellow Green, 5GY8/8, and Light Yellowish Green, 10GY8/7.

Before the calyx breaks, the bud is medium to large in size, medium-length and ovoid, with stipitate glands on the surface of the bud. Usually, stout foliaceous parts extend beyond the tip of the bud equal to one-fourth or more of its length.

As the calyx breaks, the color is between Moderate Purplish Red, 5RP5/10, and Strong Purplish Red, 7.5RP5/12. The inner surface of the sepals carry a fine tomentum. Margins of the sepals are lined with hairs.

As the first petal opens, the bud is average to large in size, of medium length and ovoid. The color on the outside of the petal is between Deep Purplish Pink, 2.5RP6/10, and Strong Purplish Pink, 5RP7/9. The edges are tinted with near Strong Purplish Red, 7.5RP4/11, while the base is near Brilliant Yellow Green, 2.5GY9/8. The inside surface of the petal is between Light Reddish Purple, 10P6/9, and Strong Purplish Pink, 5RP7/9, the base also being near Brilliant Yellow Green, 2.5GY9/8. The bud opens up well, and is not prevented from opening by cold, hot, wet or dry weather.

BLOOM

The size of the bloom when fully open is from average to large, ranging from 3½ to 4½ inches. The petalage is double, with from 25 to 30 petals, plus from 0 to 5 petaloids arranged regularly. The bloom is full and high centered to globular at first, becoming cupped to high centered. At first the petals remain somewhat loosely cupped, with tips reflexed outward, and become later at maturity more loosely cupped, with tips reflexed outward.

The petals are of medium thickness, moderately leathery, with inside slightly shiny and outside slightly satiny. The outside and intermediate petals are round to broadly obovate; inside petals are nearly round. The colors may be modified by being shaded and/or washed or tinted with other colors.

The description immediately following is of a newly opened flower of a plant grown outdoors in the month of June in Ontario, Calif.

The outer surface of outside, intermediate and inside petals was near Brilliant Greenish Yellow, 7.5Y9/8, at the base, while the remainder of the surface was between Moderate Purplish Pink, 10P7/7, and Light Purplish Pink, 2.5RP8/5. The inner surface of all petals was Near Brilliant Greenish Yellow, 7.5Y9/8, at the base, while the remainder of the inner surface was between Light Reddish Purple, 10P6/9, and Moderate Purplish Pink, 2.5RP7/8.

The description which follows was made from a rose that was open for three days. It had been grown outdoors in the month of June, at Ontario, Calif.

The outer surface of the outside petal is between Pale Purplish Pink, 10P8/5, and Pale Purplish Pink, 2.5RP9/2. The base was between white and Brilliant Yellow Green, 2.5GY9/8. The base of the inner surface of the outside petal was the same coloration as the outer surface, while the remainder of the petal was between Moderate Purplish Pink, 2.5RP7/8, and Light Purplish Pink, 2.5RP8/5.

The outer surface of the inside petal was between Pale Purplish Pink, 10P8/5, and Light Purplish Pink, 2.5RP8/5, with a base between white and Brilliant Yellow Green, 2.5GY9/8. The inner surface of the inside petal was the same coloration as that of the inner surface of the outside petal.

The general color effect of the newly opened flower is between Moderate Purplish Pink, 10P7/7, and Light Purplish Pink, 2.5RP8/5. The bloom after being three days open, gives a general color effect of near Light Purplish Pink, 2.5RP8/5. The petals persist, fading to near Pale Purplish Pink, 7.5RP9/2. They are not particularly affected by cold, hot, wet or dry weather.

The flower on the bush in the garden persists from three to five days in the month of June. Cut roses grown outdoors and kept at living-room temperatures will last from three to four days in the month of June.

REPRODUCTIVE ORGANS

There are many stamens which are arranged regularly about the pistils.

Filaments are medium-length to long and near Brilliant Greenish Yellow, 7.5Y9/8, in color. Most are with anthers.

The anthers are from medium size to large, all opening approximately at once. The color on the outer edge is near Vivid Yellow, 2.5Y8/12, while the interior is near Brilliant Greenish Yellow, 7.5Y9/8.

Pollen is abundant and near Vivid Yellow, 2.5Y8/12, in color.

There are from few to an average number of pistils, being approximately 80 in number.

The styles are moderately even, of average length and average caliper, and loosely bunched. They are between white and Brilliant Greenish Yellow, 7.5Y9/8, in color.

The stigma is near Brilliant Greenish Yellow, 7.5Y9/8.

The ovaries are usually all enclosed in the calyx.

The immature hips are of average length, globular, and with very smooth, thick, fleshy walls. They are near Strong Yellow Green, 5GY7/10, in color.

The sepals are permanent, medium-length, spear-shaped and curled. The color on the inside is between Strong Yellow Green, 5GY7/10, and Strong Yellow Green, 5GY6/8, with a gray bloom. The outside is between Strong Yellow Green, 5GY6/8, and Moderate Yellow Green, 5GY5/6, in color.

There are an average number of seeds, from 8 to 15, and these are usually medium size to large.

FOLIAGE

The compound leaves usually comprise from three to seven leaflets. They are from normal to abundant, medium size to large, heavy to somewhat leathery and semi-glossy. The leaflets are ovate, with apex acute to mucronate and base acute. The margin is doubly serrate.

The upper surface of the mature foliage is between Moderate Olive Green, 5GY4/3, the Dark Yellowish Green, 2.5G3/3, in color. The under surface is a color between Moderate Olive Green, 5GY4/3, and Dark Yellowish Green, 10GY4/5, washed heavily with gray.

The young foliage has an upper surface which is near Dark Yellowish Green, 5GY4/3, in color, washed with near Dark Red, 2.5R3/7. The under surface is near Deep Purplish Red, 10RP3/10.

The rachis is average size to heavy, the upper side being grooved and with a few stipitate glands on the edges. The underside is moderately prickly and with stipitate glands.

The stipules are medium-length to long, moderately narrow, with medium-length to long points turning out at an angle of less than 45°.

The plant displays a more than average resistance to mildew when compared to other varieties grown under comparable conditions in the same locality.

GROWTH

The plant is of upright-spreading habit, and moderately branched. It displays a moderately vigorous growth. The canes are medium to heavy in caliper.

The main stems are between Light Olive, 10Y5/5, and Moderate Yellow Green, 2.5GY5/5, in color. They bear a few large prickles which are short to medium-length, hooked downward, with a short moderately narrow base. The color is between Moderate Brown, 7.5YR4/5, and gray. There are no small prickles and no hairs.

The branches are between Light Olive, 10Y5/5, and Moderate Olive Green, 7.5GY4/4, in color. They bear a few large prickles which are short to medium-length, hooked downward, with a short moderately narrow base. The color is near Strong Yellow, 5Y7/10, with some reddish pigmentation at the base which is near Dark Red, 2.5R3/7. There are no small prickles and no hairs.

New shoots have a color between Moderate Yellow Green, 5GY5/6, and Moderate Olive Green, 5GY4/3, washed with near Dark Red, 2.5R3/7. There are from few to several large prickles which are short to medium-length, hooked slightly downward, with a short moderately narrow base. The color is near Dark Red, 2.5R3/7. There are no small prickles and no hairs.

I claim:

1. A new and distinct variety of rose plant of the hybrid Tea class, substantially as herein shown and described, being particularly characterized in the relatively uniform coloration of its light-lavender, well formed medium large blooms, which are borne mostly in clusters on long, strong stems and by a strong fragrance, a blend of citrus and tea, the plant being further characterized in its vigorous new growth and large leaves, bearing almost throughout the growing season.

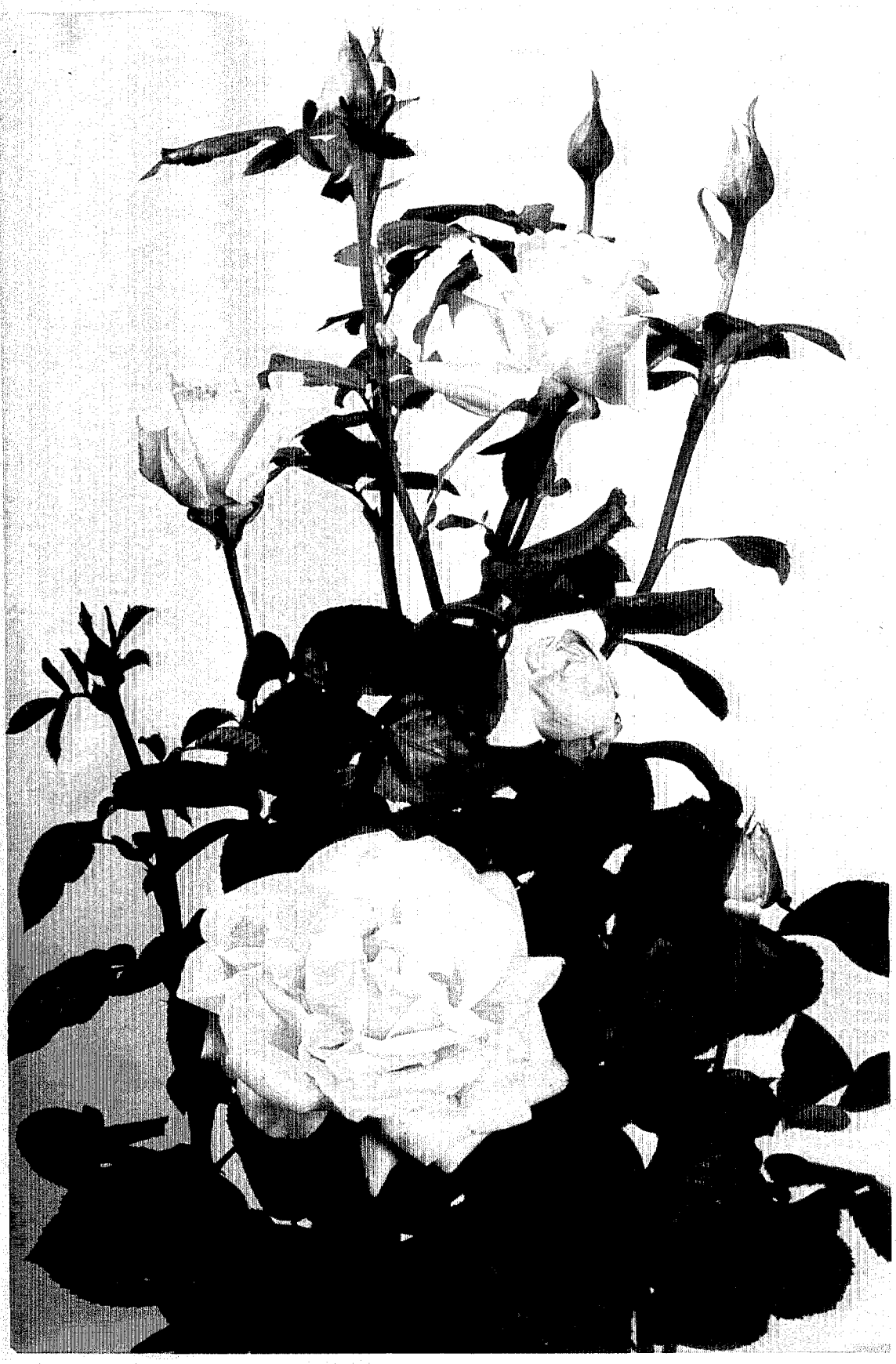

* * * * *